(12) United States Patent
Hagiwara

(10) Patent No.: US 10,194,879 B2
(45) Date of Patent: Feb. 5, 2019

(54) IMAGE PROCESSING METHOD, IMAGE PROCESSING APPARATUS AND RADIATION TOMOGRAPHIC IMAGING APPARATUS, AND PROGRAM

(71) Applicant: General Electric Company, Schenectady, NY (US)

(72) Inventor: Akira Hagiwara, Tokyo (JP)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 36 days.

(21) Appl. No.: 15/246,389

(22) Filed: Aug. 24, 2016

(65) Prior Publication Data

US 2017/0055930 A1 Mar. 2, 2017

(30) Foreign Application Priority Data

Aug. 27, 2015 (JP) ................................. 2015-168215

(51) Int. Cl.
*G06K 9/00* (2006.01)
*A61B 6/00* (2006.01)
(Continued)

(52) U.S. Cl.
CPC ............ *A61B 6/5258* (2013.01); *A61B 6/032* (2013.01); *G06T 5/002* (2013.01); *G06T 5/20* (2013.01);
(Continued)

(58) Field of Classification Search
CPC .......................................... G06T 2207/20012
See application file for complete search history.

(56) References Cited

U.S. PATENT DOCUMENTS

2007/0053485 A1* 3/2007 Kobayashi ........... A61B 5/4872
378/19
2008/0130823 A1 6/2008 Hagiwara
(Continued)

FOREIGN PATENT DOCUMENTS

| JP | 06142094 A | 5/1994 |
| JP | 2008104762 A | 5/2008 |
| WO | 2014167935 A1 | 10/2014 |

OTHER PUBLICATIONS

Joseph et al., "A Method for Correcting Bone Induced Artifacts in Computed Tomography Scanners", Journal of Computer Assisted Tomography, vol. No. 02, Issue No. 01, pp. 100-108, Jan. 1978.
(Continued)

*Primary Examiner* — Oneal R Mistry
(74) *Attorney, Agent, or Firm* — Fletcher Yoder, P.C.

(57) ABSTRACT

To reduce variability in a result of correction by beam-hardening correction in a radiation tomographic image: There is provided an image processing apparatus comprising: a first-index obtaining component configured to obtain, for each individual subregion in a beam-hardening correction-processed image representing a body region including a bone part and a soft part, a first index indicating how much beam hardening due to the bone part affects the subregion based on pixel values at a plurality of positions surrounding the subregion and a distance from the subregion; a determining component configured to determine an amount of correction on a pixel value for the subregion using the first index for the subregion; and a pixel-value correcting component configured to correct the pixel value of the subregion according to the amount of correction on the subregion.

16 Claims, 12 Drawing Sheets

(51) Int. Cl.
  *G06T 11/00* (2006.01)
  *G06T 5/00* (2006.01)
  *A61B 6/03* (2006.01)
  *G06T 5/20* (2006.01)
(52) U.S. Cl.
  CPC .. *G06T 11/005* (2013.01); *G06T 2207/10081* (2013.01); *G06T 2207/20012* (2013.01); *G06T 2207/30008* (2013.01); *G06T 2207/30016* (2013.01)

(56)  References Cited

U.S. PATENT DOCUMENTS

| | | | | |
|---|---|---|---|---|
| 2008/0152203 | A1* | 6/2008 | Bal | G06T 11/008 382/131 |
| 2009/0136107 | A1* | 5/2009 | Arnold | G06T 7/0012 382/131 |
| 2009/0221901 | A1* | 9/2009 | Yamamoto | A61B 5/055 600/410 |
| 2014/0376686 | A1* | 12/2014 | Dreiseitel | G01V 5/005 378/5 |
| 2016/0278733 | A1 | 9/2016 | Ogura et al. | |
| 2016/0287339 | A1* | 10/2016 | Bin Abdul Rahman | G09B 23/286 |
| 2017/0135665 | A1* | 5/2017 | Sandholm | A61B 6/5264 |

OTHER PUBLICATIONS

Unofficial English Translation of Japanese Search Report issued in connection with corresponding JP Application No. 2015168215 dated Jun. 6, 2017.

Unofficial English Translation of Japanese Office Action issued in connection with corresponding JP Application No. 2015168215 dated Jul. 4, 2017.

* cited by examiner

With beam-hardening correction     Without beam-hardening correction

[Tomographic image without correction]

Human head phantom     Bone-equivalent substance phantom

[Tomographic image with correction using Iterative Method]

Human head phantom        Bone-equivalent substance phantom

IMAGE PROCESSING METHOD, IMAGE PROCESSING APPARATUS AND RADIATION TOMOGRAPHIC IMAGING APPARATUS, AND PROGRAM

CROSS-REFERENCE TO RELATED APPLICATIONS

This application claims priority to Japanese Priority Application 2015-168215, entitled "Image Processing Method, Image Processing Apparatus and Radiation Tomographic Imaging Apparatus, and Program", filed on Aug. 27, 2015 and listing Akira Hagiwara as sole inventor, which is herein incorporated by reference in its entirety for all purposes.

FIELD OF THE INVENTION

The present invention relates to a technique for improving processing of reducing beam hardening artifacts in radiation tomographic images.

BACKGROUND

Radiation used in radiation tomographic imaging is continuous radiation. Therefore, as the radiation passes through a subject and attenuates, a beam hardening phenomenon occurs, wherein a high-energy portion in a radiation spectrum relatively grows and becomes hard to attenuate. In particular, in a body region including tissue like a bone part that has a higher radiation absorption coefficient, such a beam hardening phenomenon noticeably occurs. Consequently, in a reconstructed image, an effect thereof emerges as beam hardening artifacts.

Thus, when a radiation tomographic image is produced by scanning a body region including a bone part and soft tissue, what is generally called beam-hardening correction is performed for suppressing the beam hardening artifacts.

SUMMARY OF THE INVENTION

Problem to be Solved by the Invention

The size, shape, density, and the like of the bone part, however, are significantly different among individuals, and moreover, even the same person has substantially varying modes of beam hardening phenomenon depending upon the position. Such variability in the mode of beam hardening phenomenon affects the result of the correction, and may cause undercorrection or overcorrection depending upon the position.

For example, focusing upon a border between a bone part and soft tissue in a head, there sometimes is a dispersed mixture of regions that experience insufficient correction processing and are rendered with higher CT value (or in more white) than in other regions, and other regions, causing variability. As such, beam hardening artifacts have individual differences, and moreover, there is variability such that correction thereon is sufficient in some regions and insufficient in other regions, even in the same image.

In such circumstances, there is a need for a technique capable of reducing variability in the result of correction by beam-hardening correction in a radiation tomographic image.

Means for Solving the Problem

The invention, in its first aspect, provides an image processing method causing a computer to execute:

a first-index obtaining step of obtaining, for each individual subregion in a beam-hardening correction-processed image representing a body region including a bone part and a soft part, a first index indicating how much beam hardening due to said bone part affects said subregion based on pixel values at a plurality of positions surrounding said subregion and a distance from said subregion;

a determining step of determining an amount of correction on a pixel value for said subregion using the first index for said subregion; and a pixel-value correcting step of correcting the pixel value of said subregion according to the amount of correction on said subregion.

The invention, in its second aspect, provides an image processing apparatus comprising:

first-index obtaining means for obtaining, for each individual subregion in a beam-hardening correction-processed image representing a body region including a bone part and a soft part, a first index indicating how much beam hardening due to said bone part affects said subregion based on pixel values at a plurality of positions surrounding said subregion and a distance from said subregion;

determining means for determining an amount of correction on a pixel value for said subregion using the first index for said subregion; and pixel-value correcting means for correcting the pixel value of said subregion according to the amount of correction on said subregion.

The invention, in its third aspect, provides the image processing apparatus as described regarding the second aspect, wherein:

said first-index obtaining means obtains as said first index a value containing as components, for each of a plurality of positions surrounding said subregion, a first value growing according to a pixel value at said position, and a second value growing according to a distance from said subregion to said position.

The invention, in its fourth aspect, provides the image processing apparatus as described regarding the third aspect, wherein:

said first-index obtaining means obtains, for each of a plurality of positions surrounding said subregion, a multiplied value of said first value with said second value, and obtains as said first index a value containing as a component an added value of said multiplied value obtained for each of said plurality of positions.

The invention, in its fifth aspect, provides the image processing apparatus as described regarding the fourth aspect, wherein:

said first-index obtaining means obtains, for each of a plurality of positions surrounding said subregion, a product of said first value with said second value, and obtains as said first index a value containing as a component a sum of said product obtained for each of said plurality of positions.

The invention, in its sixth aspect, provides the image processing apparatus as described regarding any one of the second through fifth aspects, further comprising:

difference obtaining means for obtaining, for each said individual subregion, a difference between a pixel value of said subregion and a reference value for pixel values representing said soft part; and second-index obtaining means for obtaining, for each said individual subregion, a second index indicating a degree of a correlation between a change of said first index in a direction passing through said subregion and a change of said difference in said direction, wherein said determining means determines an amount of correction on a pixel value for said subregion based on the second index for said subregion.

The invention, in its seventh aspect, provides the image processing apparatus as described regarding the sixth aspect, wherein:

said determining means determines as said amount of correction a product of a value according to the second index for said subregion and said difference for said subregion.

The invention, in its eighth aspect, provides the image processing apparatus as described regarding the seventh aspect, wherein:

the reference value for pixel values representing said soft part is an average of pixel values in a region representing said soft part in said image.

The invention, in its ninth aspect, provides the image processing apparatus as described regarding the seventh aspect, wherein:

the reference value for pixel values representing said soft part is a representative value of pixel values considered to correspond to said soft part.

The invention, in its tenth aspect, provides the image processing apparatus as described regarding any one of the sixth through ninth aspects, further comprising:

first smoothing processing means for applying smoothing processing to a distribution of said first index in said image and a distribution of said difference in said image, wherein said second-index obtaining means obtains said second index based on a correlation between a change of said first index to which said smoothing processing has been applied in said direction and a change of said difference to which said smoothing processing has been applied in said direction.

The invention, in its eleventh aspect, provides the image processing apparatus as described regarding the tenth aspect, wherein:

said second-index obtaining means obtains said second index so that it has a greater value for higher said correlation.

The invention, in its twelfth aspect, provides the image processing apparatus as described regarding any one of the second through eleventh aspects, further comprising:

correction upper-limit value determining means for determining an upper-limit value of the amount of correction for said subregion according to a magnitude of the first index for said subregion, wherein said pixel-value correcting means corrects a pixel value of said subregion so that the amount of correction does not exceed an upper-limit value determined for said subregion.

The invention, in its thirteenth aspect, provides the image processing apparatus as described regarding any one of the second through twelfth aspects, further comprising:

second smoothing processing means for applying smoothing processing to a distribution of said amount of correction in said image, wherein said pixel-value correcting means makes correction using an amount of correction to which said smoothing processing has been applied.

The invention, in its fourteenth aspect, provides the image processing apparatus as described regarding the tenth, eleventh or thirteenth aspect, wherein:

said smoothing processing is averaging/smoothing processing.

The invention, in its fifteenth aspect, provides the image processing apparatus as described regarding any one of the second through fourteenth aspects, wherein:

said image is an image reconstructed based on projection data for said body region to which beam-hardening correction processing has been applied.

The invention, in its sixteenth aspect, provides the image processing apparatus as described regarding any one of the second through fifteenth aspects, wherein:

said beam-hardening correction processing uses an algorithm designed to correct beam hardening due to the bone part.

The invention, in its seventeenth aspect, provides the image processing apparatus as described regarding any one of the second through sixteenth aspects, wherein:

said body region is a head.

The invention, in its eighteenth aspect, provides the image processing apparatus as described regarding any one of the second through seventeenth aspects, wherein:

said subregion is a region corresponding to a single pixel.

The invention, in its nineteenth aspect, provides a radiation tomographic imaging apparatus comprising the image processing apparatus as described regarding any one of the second through eighteenth aspects.

The invention, in its twentieth aspect, provides a program for causing a computer to function as the means in the image processing apparatus as described regarding any one of the second through eighteenth aspects.

Effect of the Invention

According to the invention in the aspects described above, in a beam-hardening correction-processed image representing a body region including a bone part and soft tissue, each individual subregion is sequentially defined as a region of interest, and a first index indicating how much beam hardening due to the bone part affects the region of interest is obtained based on pixel values at a plurality of positions surrounding the defined region of interest and a distance from the region of interest, an amount of correction on the pixel value for the region of interest is determined using the first index for the region of interest, and the pixel value of the region of interest is corrected according to the amount of correction; therefore, for a portion in which mere conventional beam-hardening correction processing in a projection data space cannot fully correct the effect, the degree of the effect of beam hardening may be estimated with reference to information on the amount or closeness of the bone part present in the surrounding portion, and additional correction may be further applied to the pixel value using a result of the estimation, so that variability in the result of correction by beam-hardening correction may be reduced in a radiation tomographic image.

MODES FOR CARRYING OUT THE INVENTION

Now an embodiment of the invention will be described hereinbelow. It should be noted that the invention is not hereby limited.

Figure 1:
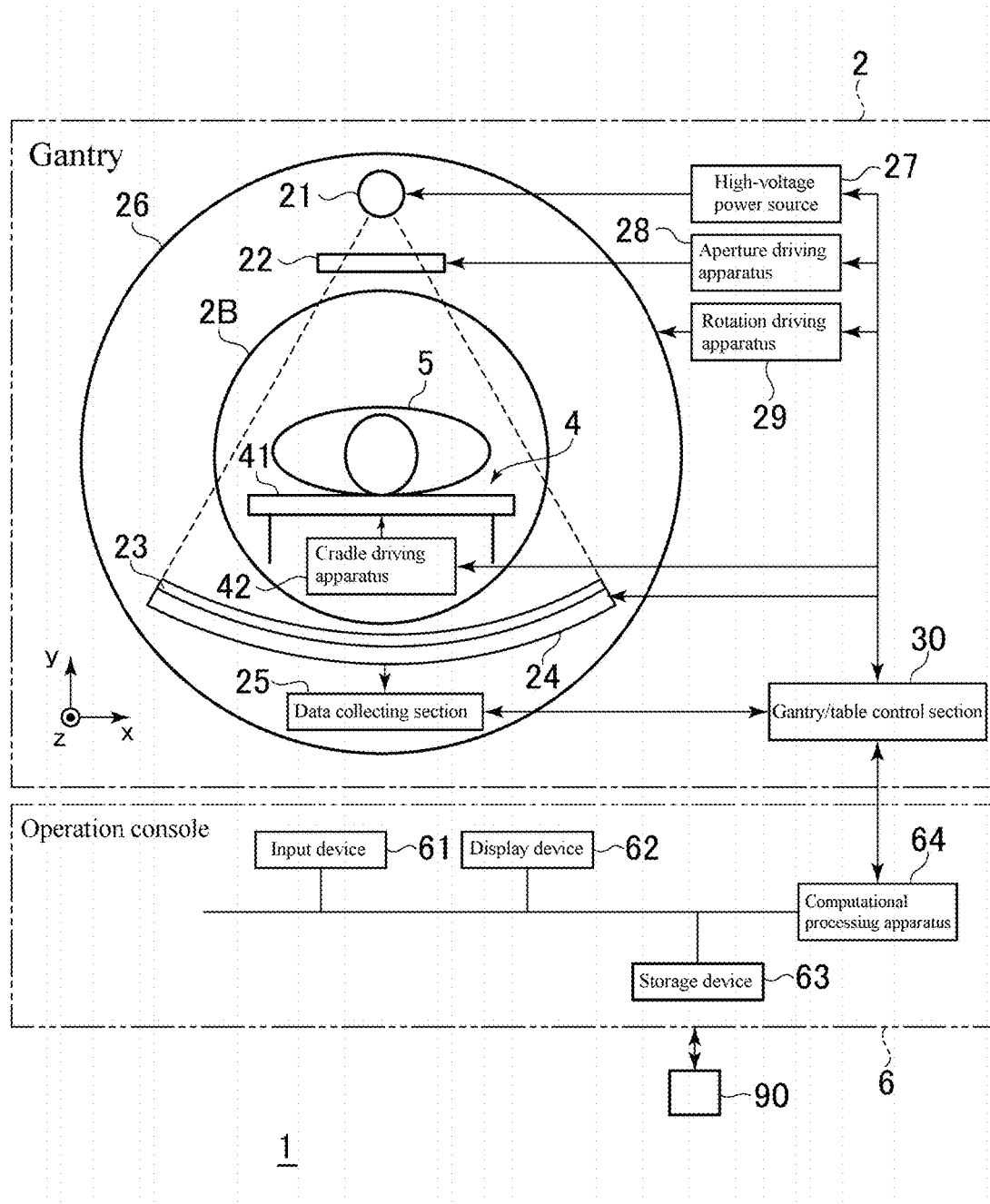
FIG. 1 A diagram schematically showing a hardware configuration of an X-ray CT apparatus in accordance with the present embodiment.

FIG. 1 is a diagram schematically showing a hardware configuration of an X-ray CT apparatus (X-ray Computed Tomography system) in accordance with the present embodiment.

As shown in FIG. 1, the X-ray CT apparatus 1 comprises a gantry 2, an imaging table 4, and an operation console 6.

The gantry 2 has an X-ray tube 21, an aperture 22, a collimator device 23, an X-ray detector 24, a data collecting section 25, a rotating section 26, a high-voltage power source 27, an aperture driving apparatus 28, a rotation driving apparatus 29, and a gantry/table control section 30.

The X-ray tube 21 and X-ray detector 24 are disposed to face each other across a bore 2B.

The aperture 22 is disposed between the X-ray tube 21 and bore 2B. X-rays emitted from an X-ray focus of the X-ray tube 21 toward the X-ray detector 24 are shaped into a fan beam or a cone beam.

The collimator device 23 is disposed between the bore 2B and X-ray detector 24. The collimator device 23 removes scatter rays impinging upon the X-ray detector 24.

The X-ray detector 24 has a plurality of X-ray detector elements two-dimensionally arranged in a direction (referred to as channel direction) of the span of the fan-shaped X-ray beam emitted from the X-ray tube 21 and a direction (referred to as row direction) of the thickness. Each respective X-ray detector element detects X-rays passing through a subject 5 laid in the bore 2B, and outputs an electric signal depending upon the intensity thereof. The subject 5 is an animate being, such as, for example, a human or an animal.

The data collecting section 25 receives the electric signal output from each X-ray detector element in the X-ray detector 24, and converts it into X-ray data for collection.

The rotating section 26 is rotatably supported around the bore 2B. The rotating section 26 has the X-ray tube 21, aperture 22, collimator device 23, X-ray detector 24, and data collecting section 25 mounted thereon.

The imaging table 4 has a cradle 41 and a cradle driving apparatus 42. The subject 5 is laid on the cradle 41. The cradle driving apparatus 42 moves the cradle 41 into/out of the bore 2B, i.e., an imaging volume, in the gantry 2.

The high-voltage power source 27 supplies high voltage and current to the X-ray tube 21.

The aperture driving apparatus 28 drives the aperture 22 and modifies the shape of its opening.

The rotation driving apparatus 29 rotationally drives the rotating section 26.

The gantry/table control section 30 controls several apparatuses and sections in the gantry 2, the imaging table 4, and the like.

The operation console 6 accepts several kinds of operation from an operator. The operation console 6 has an input device 61, a display device 62, a storage device 63, and a computational processing apparatus 64. In the present embodiment, the operation console 6 is constructed from a computer.

As shown in FIG. 1, a direction of the body axis of the subject 5, i.e., a direction of transportation of the subject 5 by the imaging table 4, will be referred to herein as z-direction. Moreover, a vertical direction will be referred to as y-direction, and a horizontal direction orthogonal to the y- and z-directions as x-direction.

Next, a function of the X-ray CT apparatus in accordance with the present embodiment will be described. The X-ray CT apparatus in accordance with the present embodiment has a function of reducing variability in a result of correction by conventional beam-hardening correction. Its fundamental concept is as follows: conventional beam-hardening correction is first performed. In a resulting beam-hardening corrected tomographic image, each pixel is sequentially defined as a pixel of interest, and a relationship between the distance from the pixel of interest for its surrounding pixels and the pixel values (CT values) thereof is closely investigated. From a behavior of a change in the pixel value thus obtained, an evaluation is made as to whether each pixel is a beam hardening artifact or represents partial bleeding or a contrast effect by a contrast medium. Then, from a result of the evaluation, a decision about variability in beam hardening artifacts is made for each pixel or image subregion, and additional correction is applied to an undercorrected pixel/image region to reduce variability in correction for each pixel or image subregion. Consequently, beam-hardening correction may be achieved with more stable quality.

Figure 2:
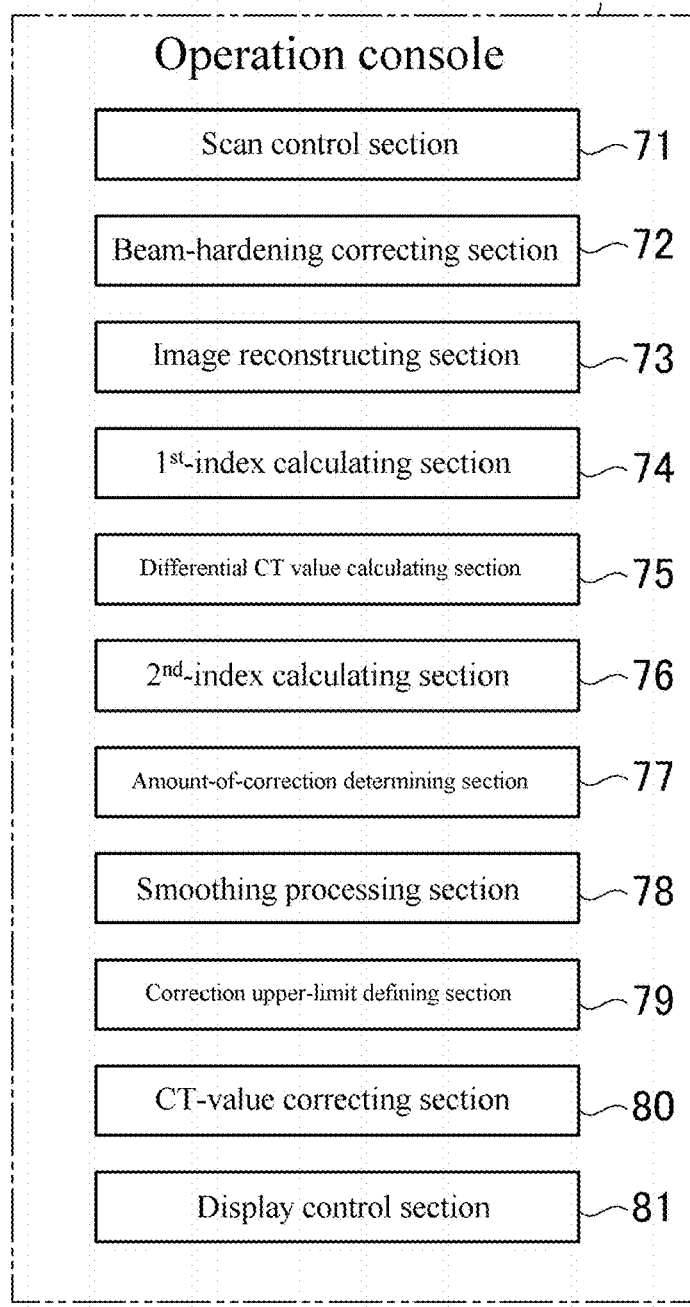
FIG. 2 A functional block diagram of the operation console in the X-ray CT apparatus in accordance with the present embodiment.

FIG. 2 is a functional block diagram of the operation console in the X-ray CT apparatus in accordance with the present embodiment.

The operation console 6 in the X-ray CT apparatus in accordance with the present embodiment has, as functional blocks for implementing the function described above, a scan control section 71, a beam-hardening correcting section 72, an image reconstructing section 73, a first-index calculating section 74, a differential CT value calculating section 75, a second-index calculating section 76, an amount-of-correction determining section 77, a smoothing processing section 78, a correction upper-limit defining section 79, a CT-value correcting section 80, and a display control section 81.

The first-index calculating section 74 is an example of the first-index obtaining means in the invention. The differential CT value calculating section 75 is an example of the difference obtaining means in the invention. The second-index calculating section 76 is an example of the second-index obtaining means in the invention. The amount-of-correction determining section 77 is an example of the determining means in the invention. The smoothing processing section 78 is an example of the first and second smoothing processing means in the invention. The correction upper-limit defining section 79 is an example of the defining means in the invention. The CT-value correcting section 80 is an example of the pixel-value correcting means in the invention.

Moreover, the operation console 6 functions as each functional block by the computational processing apparatus 64 executing a specified program. The specified programs are stored in, for example, the storage device 63 or an externally connected storage device or medium 90.

The scan control section 71 controls the gantry/table control section 30 to perform a scan in response to an operation by the operator.

The beam-hardening correcting section 72 applies beam-hardening correction by a specified algorithm to projection data in a plurality of views resulting from the scan.

The image reconstructing section 73 reconstructs a tomographic image based on the projection data using a reconstruction function. The image reconstructing section 73 reconstructs a tomographic image based on original collected projection data or reconstructs a beam-hardening corrected tomographic image based on beam-hardening corrected projection data depending upon a request from the beam-hardening correcting section 72.

The first-index calculating section 74 calculates a first index indicating how much the effect of beam hardening is present for each individual pixel constituting the beam-hardening corrected tomographic image.

The differential CT value calculating section 75 calculates, for each individual pixel constituting the beam-hardening corrected tomographic image, a difference (which will be sometimes referred to as differential CT value hereinbelow) between a CT value of that pixel and a reference value (which will be sometimes referred to as reference CT value hereinbelow) of CT values representing soft tissue.

The second-index calculating section 76 calculates, for each individual pixel constituting the beam-hardening corrected tomographic image, a second index indicating a degree of certainty that the pixel is a beam hardening artifact based on a correlation between a change of the first index in a direction containing that pixel and a change of the differential CT value.

The amount-of-correction determining section 77 determines, for each individual pixel constituting the beam-hardening corrected tomographic image, an amount of correction on the CT value based on the second index for that pixel.

The smoothing processing section 78 applies smoothing processing to a spatial distribution of the first index, differential CT value or amount of correction for each pixel in the beam-hardening corrected tomographic image.

The correction upper-limit defining section 79 defines, for each pixel in the beam-hardening corrected tomographic image, a correction upper-limit value for that pixel using the first index for that pixel. The correction upper-limit value is a value representing an upper limit of the amount of correction.

The CT-value correcting section 80 additionally applies, for each pixel in the beam-hardening corrected tomographic image, shift correction to the CT value depending upon the amount of correction on that pixel. At this time, the amount of correction is prevented from exceeding the correction upper-limit value.

The display control section 81 controls the display device 62 to display the additionally corrected tomographic image on its screen.

Next, the flow of processing in the X-ray CT apparatus in accordance with the present embodiment will be described.

Figure 3:
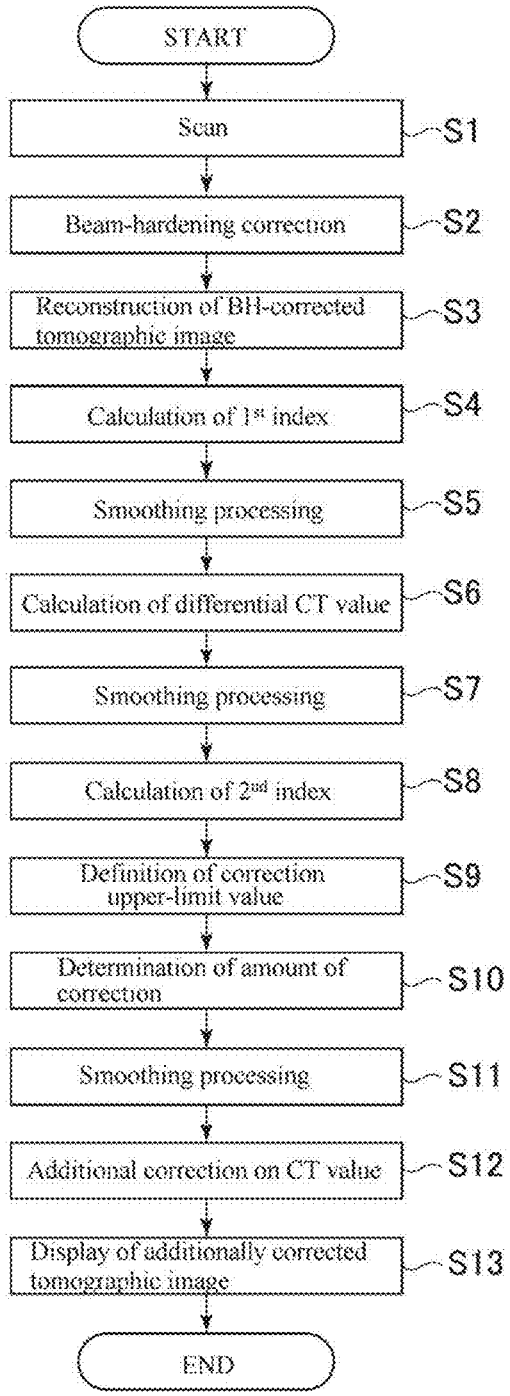
FIG. 3 A flow chart showing the flow of processing in the X-ray CT apparatus in accordance with the present embodiment.

FIG. 3 is a flow chart showing the flow of processing in the X-ray CT apparatus in accordance with the present embodiment.

At Step S1, a scan is performed. Specifically, the scan control section 71 controls the gantry/table control section 30 to perform a scan on a head 5h.

Figure 4:
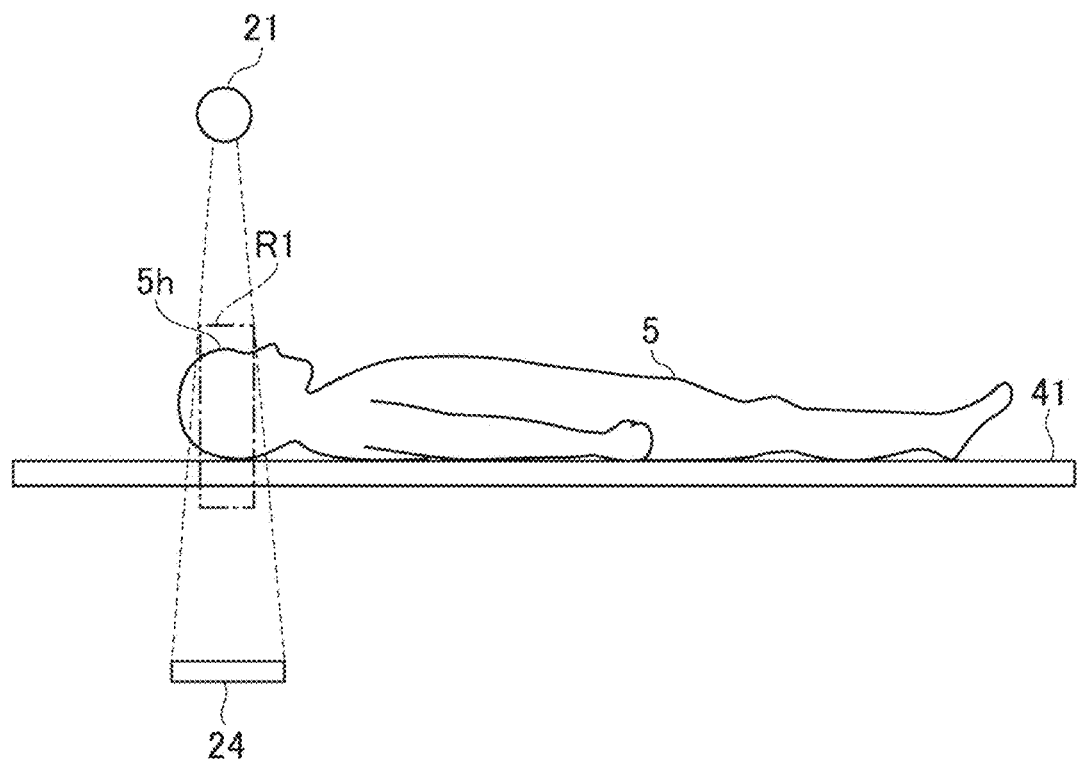
FIG. 4 A diagram showing a state in which a head of a subject is scanned in the present embodiment.

FIG. 4 is a diagram schematically showing a state in which the head 5h of the subject is scanned in the present embodiment. In this example, a scan is performed on an imaging volume R1 including the head 5h of the subject 5 laid on the cradle 41, as shown in FIG. 4. The scan is performed by emitting X-rays from the X-ray focus of the X-ray tube 21 onto the subject 5 while rotating the X-ray tube 21 and X-ray detector 24 around the subject 5. Moreover, the scan is assumed to be what is generally called a half scan in which a view angle range is 180 degrees plus a fan angle α of the X-ray beam. On performing the scan, projection data in a plurality of views are collected for each of a plurality of slices formed by slicing the imaging volume in the z-axis direction caused by the arrangement of the X-ray detector elements in the X-ray detector 24.

At Step S2, beam-hardening correction is performed. Specifically, the beam-hardening correcting section 72 applies beam-hardening correction to the projection data obtained by the scan at Step S1. Now the beam-hardening correction will be described in detail.

Figure 5:
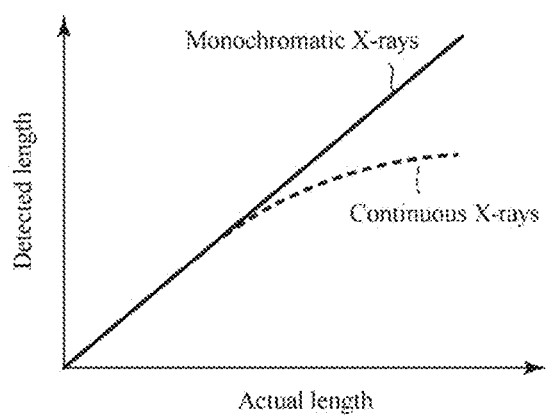
FIG. 5 A diagram for explaining the nonlinear property of beam hardening.

The beam-hardening correction uses a correction method involving, for example, approximating the nonlinear property of beam hardening, as shown in FIG. 5, by a high-order, such as third- to fourth-order, polynomial, and then, applying inverse transformation for replacement with linear data. The approximation by a high-order polynomial is achieved by calibrating coefficients in the high-order polynomial by the attenuation property of a few kinds of phantom or a few kinds of transmission path length, and determining the coefficients.

For the formula of correction, one calculated with reference to water is generally used because a major part of a human body is close to water.

Figure 6:
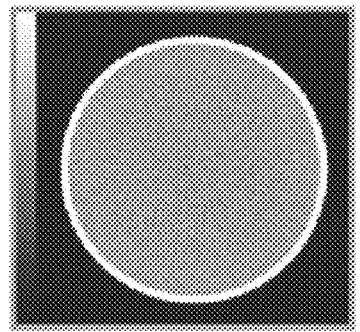
FIG. 6 A graphical depiction showing an effect of correction of beam-hardening correction in a water phantom.
Figure 6:
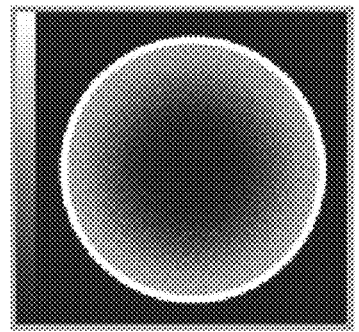

FIG. 6 shows an effect of correction in a water phantom. It can be seen that a tomographic image without beam-hardening correction has lower CT values on the central side of the phantom as compared with those on the outer side. On the other hand, it can be seen that a tomographic image with beam-hardening correction has homogeneous CT values for representing water, and has generally the same CT values between the center side and outer side of the phantom.

The beam-hardening correction method described above is called first-order beam-hardening correction, and its reference substance is generally water. A human body, however, has bones having a significantly different absorption coefficient from that of water. Accordingly, mere beam-hardening correction on water cannot fully correct the effect of beam hardening by the bones. Representative of the effects are shading in the inside of the skull and dark band-like artifacts appearing between the temporal bones in head imaging.

Figure 7:
FIG. 7 A graphical depiction showing images of a human head phantom and a bone-equivalent substance phantom in which the effect of beam hardening manifests itself.
Figure 7:
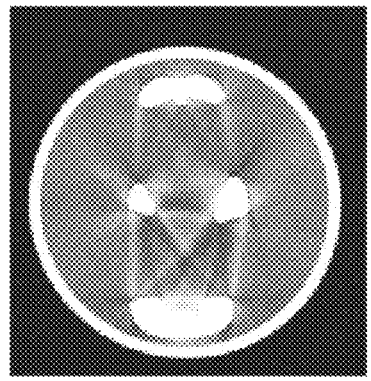

FIG. 7 shows an image (left) of a human head phantom and an image (right) of a bone-equivalent substance phantom, where these effects manifest themselves. In either image, shading and band-like artifacts significantly manifest themselves in the vicinity of the bone-equivalent substance.

Assuming that respective X-ray transmission lengths of soft tissue and of a bone part are known, it is possible to achieve more accurate beam-hardening correction by providing two beam-hardening correction tables. A technique implementing such correction was published in 1978 by P. M. Joseph, et al. as an Iterative Method involving repeating image reconstruction.

Figure 8:
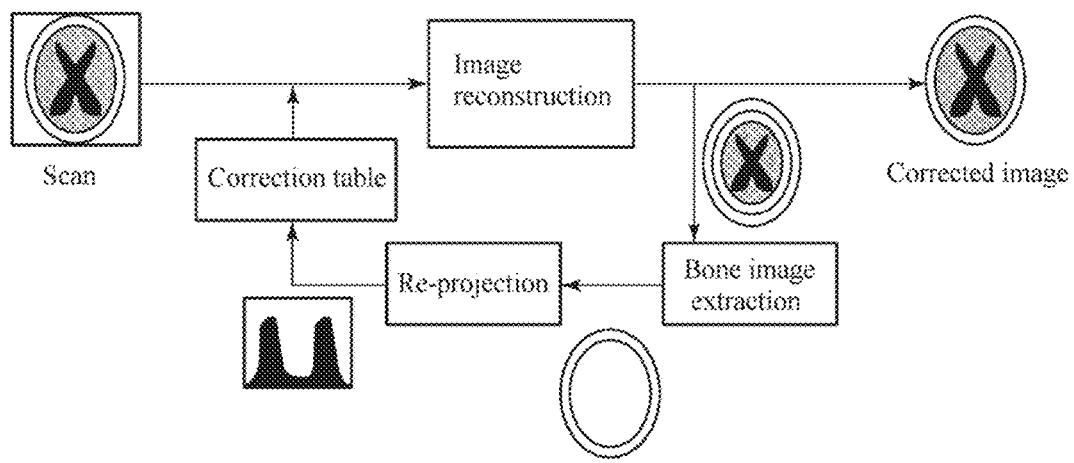
FIG. 8 A diagram showing a concept of correction processing by an iterative method.

FIG. 8 shows a concept of correction processing by the Iterative Method. Only bones are extracted from a first-time reconstructed image using a threshold of the CT value, the bone image is re-projected to thereby obtain an X-ray transmission length of the bone, and an error caused by beam hardening depending upon the transmission length of the bone is obtained. Next, the original data is corrected by a correction table, and then, second-time reconstruction is performed, whereby an intended image may be obtained.

Figure 9:
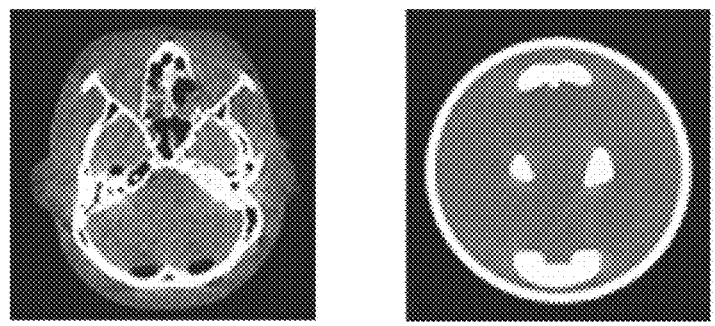
FIG. 9 A graphical depiction showing an effect of the correction by the iterative method.

FIG. 9 shows an image (left) of the human head phantom and an image (right) of the bone-equivalent substance phantom when correction according to the Iterative Method is used. It can be seen by comparing them with the examples without correction in FIG. 7 that artifacts from the bone part have been corrected.

The beam-hardening correction in the present example uses correction according to the Iterative Method described above, which is capable of correcting beam hardening caused by a bone part. It should be noted that beam-hardening correction is not limited to that according to the Iterative Method, and several kinds of correction may be employed.

At Step S3, a beam-hardening corrected tomographic image is reconstructed. Specifically, the image reconstructing section 73 reconstructs a beam-hardening corrected tomographic image based on the beam-hardening corrected projection data.

At Step S4, a first index B is calculated. Specifically, the first-index calculating section 74 calculates, for each pixel in a region corresponding to soft tissue in the beam-hardening corrected tomographic image, a first index B indicating an estimated level of the degree of an experienced effect of beam hardening. Identification of the region corresponding to soft tissue is achieved by using, for example, thresholding by the CT value.

Figure 10:
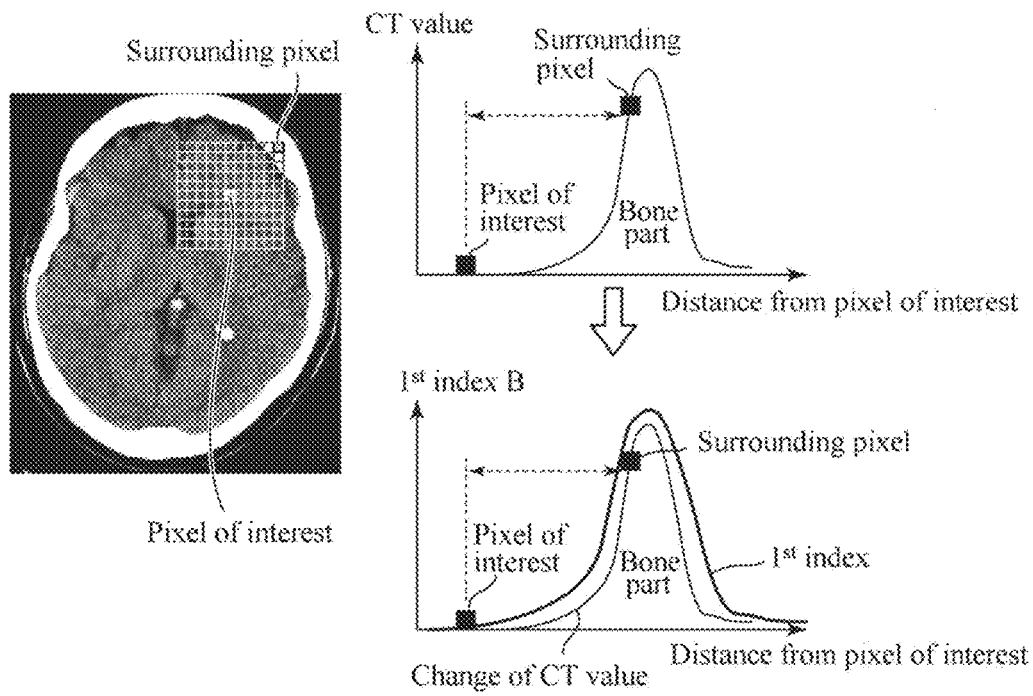
FIG. 10 A diagram showing a concept of a first index.

FIG. 10 shows a concept of the first index.

A first index B for a certain specific pixel of interest is roughly calculated by a sum of an multiplied value (referred to as degree of bone proximity) of a value derived from a CT value of its surrounding pixel and a distance thereof from the pixel of interest.

The following equations represent exemplary formulae for calculating the first index B:

$$B(x, y) = \sum_{i=1}^{n} \text{Bone\_index}(x_i, y_i) \quad (1\text{-}1)$$

$$\text{Bone\_index}(x_i, y_i) = P(x_i, y_i) \cdot \text{wght\_dist}(x_i, y_i) \quad (1\text{-}2)$$

$$\text{wght\_dist}(x_i, y_i) = 1 - \text{pix\_dist}(x_i, y_i)/\text{specific\_value} \quad (1\text{-}3)$$

$$\text{pix\_dist}(x_i, y_i) = \sqrt{(x - x_i)^2 + (y - y_i)^2} \quad (1\text{-}4)$$

$$\text{specific\_value} = \text{a constant} \quad (1\text{-}5)$$

where (x, y) denote coordinates of the pixel of interest, and $(x_i, y_i)$ denote coordinates of a surrounding pixel.

Accordingly, the higher the CT value P of a surrounding pixel is, and the closer it lies to a pixel having a CT value P equivalent to a bone part, the higher the first index B is. Moreover, the surrounding pixel is omnidirectionally checked, so that for a pixel of interest surrounded in its periphery by a bone part, a high first index B for the pixel in such a region results even when its degree of bone proximity in one direction is not so high, because the first index B is represented by a sum of the degree of bone proximity in several directions.

At Step S5, smoothing processing is performed. Specifically, the smoothing processing section 78 applies smoothing processing to a spatial distribution of the first index B calculated at Step S4. The smoothing processing is achieved by using, for example, a 3-by-3 or 5-by-5 smoothing filter.

At Step S6, a differential CT value Pd is calculated. Specifically, the differential CT value calculating section 75 calculates, for each pixel in a region corresponding to soft tissue in the beam-hardening corrected tomographic image, a differential CT value Pd, which is a difference between a CT value P of that pixel and a reference CT value P_soft for soft tissue.

At Step S7, smoothing processing is performed. Specifically, the smoothing processing section 78 applies smoothing processing to a spatial distribution of the differential CT value Pd calculated at Step S6.

At Step S8, a second index S is calculated. Specifically, the second-index calculating section 76 calculates, for each pixel in a region corresponding to soft tissue in the beam-hardening corrected tomographic image, a second index S indicating the degree of certainty that the pixel is a beam hardening artifact. Here, the second index S is calculated as a value representing a height of correlation between a positional change of the smoothing-processed first index B and a positional change of the smoothing-processed differential CT value Pd in a direction containing that pixel of interest.

Figure 11:
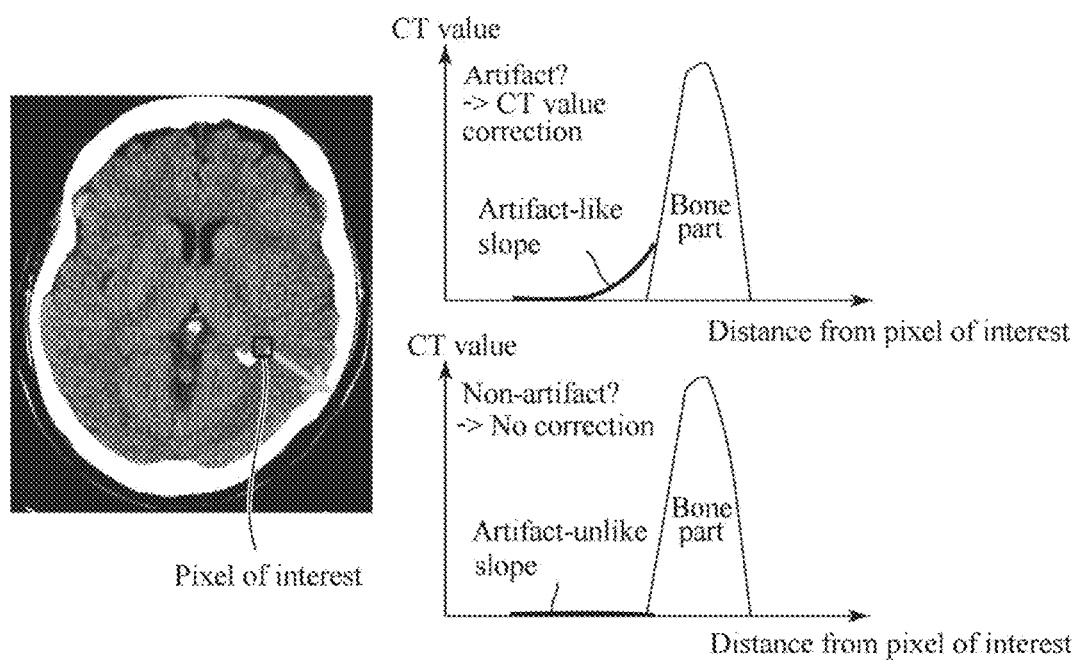
FIG. 11 A diagram showing a concept of a second index.

FIG. 11 shows a concept of the second index. The second index S for a certain specific pixel of interest is roughly calculated by a value representing a height of correlation between a positional slope (gradient) of the first index B and a positional slope (gradient) of the differential CT value Pd in a pixel row containing the pixel of interest.

The following equations represent exemplary formulae for calculating the second index S:

$$S(x, y) = \left(\sum_{y'=y-n}^{y+n} \sum_{x'=x-n}^{x+n} \frac{Pd(x', y') - Pd(x, y)}{B(x', y') - B(x, y)} \times Cp(x', y')\right) \Big/ Cind(x, y) \quad (2\text{-}1)$$

$$Cind(x, y) = \sum_{y'=y-n}^{y+n} \sum_{x'=x-n}^{x+n} Cp(x', y') \quad (2\text{-}2)$$

$$Cp(x', y') = \begin{cases} 1, & \text{if } \frac{Pd(x', y') - Pd(x, y)}{B(x', y') - B(x, y)} > 0 \\ 0, & \text{if } \frac{Pd(x', y') - Pd(x, y)}{B(x', y') - B(x, y)} \le 0 \end{cases} \quad (2\text{-}3)$$

$$Pd(x, y) = P(x, y) - P\_\text{soft} \quad (2\text{-}4)$$

where P_soft denotes a reference CT value for soft tissue, and Pd(x, y) denotes a differential CT value of the pixel of interest.

The reference CT value P_soft for soft tissue may be defined by, for example, an average of the CT values P of a plurality of pixels representing soft tissue in a corrected tomographic image. The soft tissue may be identified by thresholding processing on the CT value P. The reference CT value P_soft for soft tissue may also be defined by, for example, a representative value of the CT values P that may be considered to correspond to soft tissue from an empirical rule.

It may be generally considered that the closer the differential CT value Pd of the pixel of interest to the CT value representing a bone part in the corrected tomographic image, and the higher the CT value P representing a bone part, the higher the likelihood that the pixel of interest is a beam hardening artifact. Accordingly, in a pixel row containing the pixel of interest, a higher correlation between the positional slope of the first index B and the positional slope of the differential CT value Pd results in a higher likelihood that the pixel of interest is a beam hardening artifact.

On the other hand, as indicated in the lower part of the drawing, a lower correlation therebetween results in a lower likelihood that the pixel of interest is a beam hardening artifact.

Figure 12:
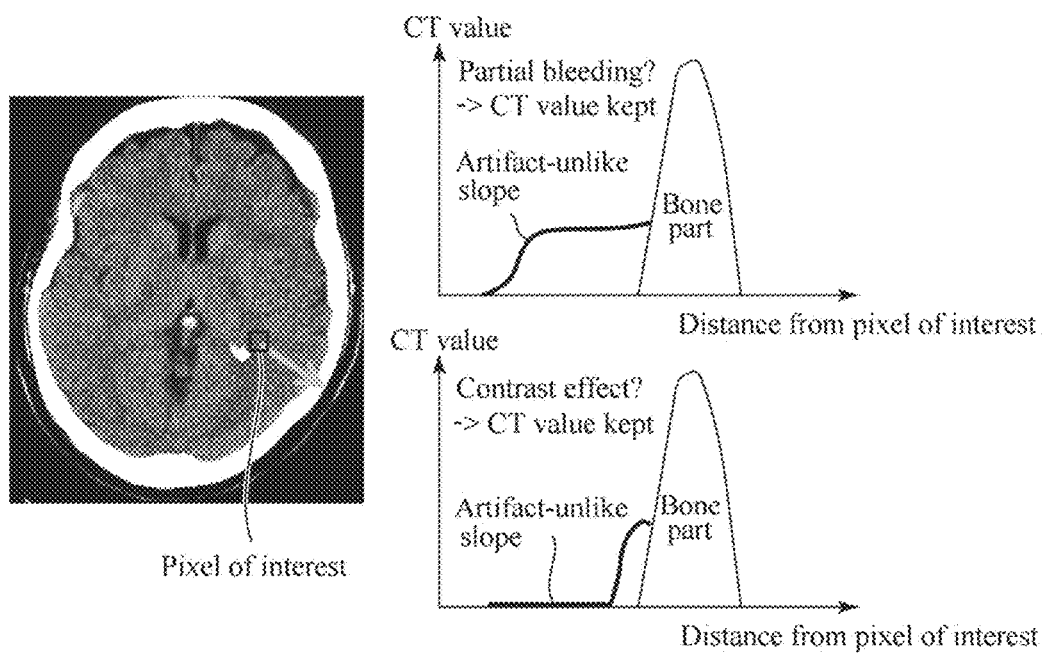
FIG. 12 A diagram showing a continuation of the concept of the second index.

FIG. 12 shows a continuation of the concept of the second index. In the case that the CT value P is partially high due to bleeding or a contrast effect of the contrast medium in the corrected tomographic image, the correlation between the positional slope of the first index B and the positional slope of the differential CT value Pd is low in such a region.

It may thus be considered that the second index S for a certain specific pixel of interest represents the degree of certainty that the pixel is a beam hardening artifact.

At Step S9, a correction upper-limit value is defined. Specifically, the correction upper-limit defining section 79 defines a correction upper-limit value ΔP_cap for each pixel in a region corresponding to soft tissue in the beam-hardening corrected tomographic image. The correction upper-limit value is defined based on the original first index B or smoothing-processed first index B calculated for that pixel of interest as a value that increases for a greater value of the index.

Figure 13:
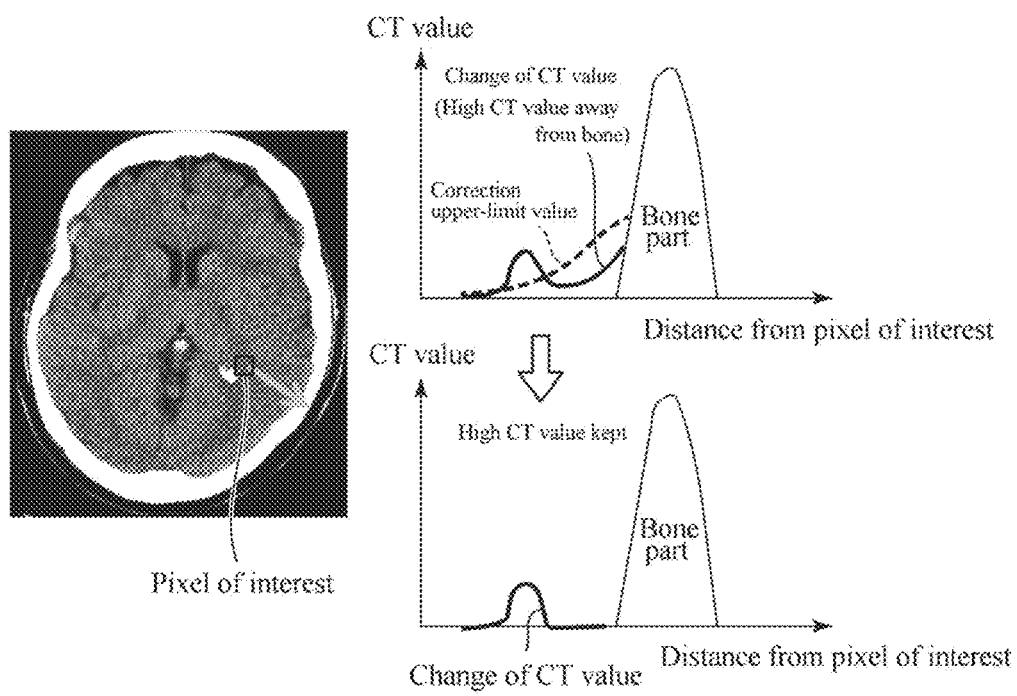
FIG. 13 A diagram showing a concept of a correction upper-limit value.

FIG. 13 shows a concept of the correction upper-limit value. The upper-limit value for the amount of correction is defined as a function for suppressing overcorrection. By defining an optimal correction upper-limit value for each region in synchronization with the first index B, more proper correction may be expected.

Figure 14:
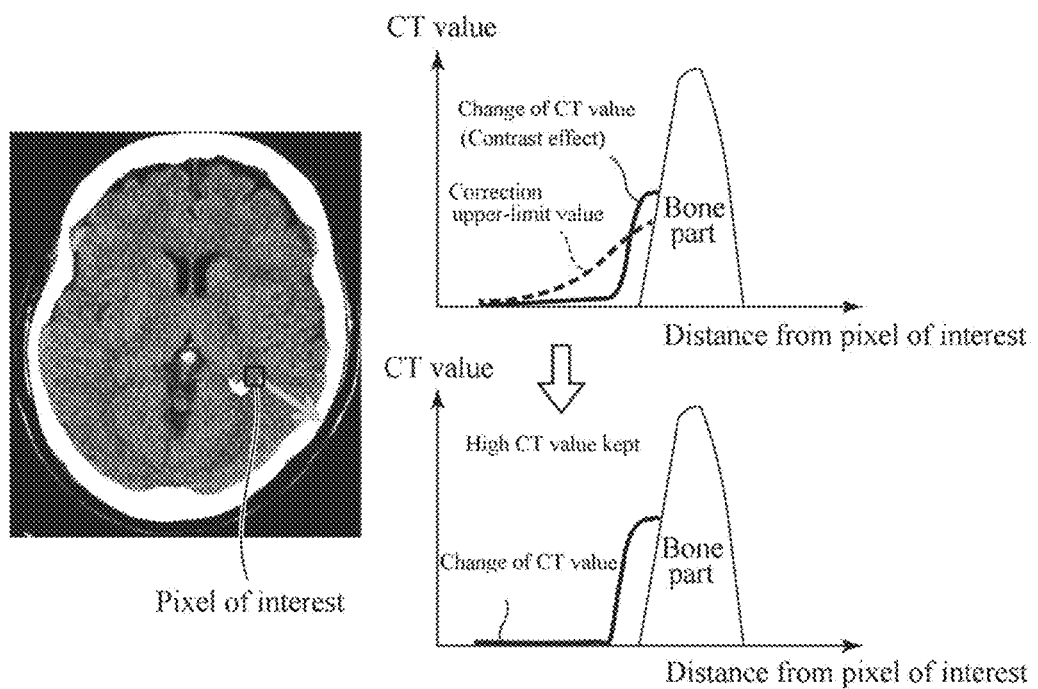
FIG. 14 A diagram showing a continuation of the concept of the correction upper-limit value.

FIG. 14 shows a continuation of the concept of the correction upper-limit value. It may be understood referring to FIG. 14 that a risk that a rise of the CT value P due to partial bleeding or a local contrast effect is misrecognized as beam hardening artifact to be corrected is reduced.

The following equation represents an exemplary formula for calculating the correction upper-limit value ΔP_cap:

$$\Delta P\_cap(x,y) = B(x,y) \times Pd(x,y) \times a \qquad (3\text{-}1)$$

where a is an arbitrary constant.

At Step S10, an amount of correction is determined. Specifically, the amount-of-correction determining section 77 determines an amount of correction ΔP on the CT value for each pixel in a region corresponding to soft tissue in the beam-hardening corrected tomographic image. The amount-of-correction determining section 77 determines, for example, a weighting factor wght_ind for a pixel of interest based on the second index S calculated for the pixel of interest, and sets a multiplied value of the weighting factor wght_ind for the pixel of interest with the differential CT value Pd as the amount of correction ΔP. It should be noted that the amount of correction ΔP for the pixel of interest should be set in a range not exceeding the correction upper-limit value ΔP_cap defined for that pixel of interest.

The following equation represents an exemplary formula for calculating the amount of correction ΔP:

$$\Delta P = Pd(x, y) \times \text{wght\_ind}(x, y) \qquad (4\text{-}1)$$

$$\text{wght\_ind}(x, y) = \qquad (4\text{-}2)$$
$$\begin{cases} 0, & \text{if } S(x, y) \geq S\_max \\ 1 - \dfrac{S(x, y) - S\_mid}{S\_max - S\_mid}, & \text{if } S\_mid \leq S(x, y) < S\_max \\ \dfrac{S(x, y) - S\_mid}{S\_max - S\_mid}, & \text{if } S\_min \leq S(x, y) < S\_mid \\ 0, & \text{if } S(x, y) \leq S\_max \end{cases}$$

where S_max, S_mid, and S_min denote a maximum value, a middle or median value, and a minimum value of the second index S in the corrected tomographic image, respectively.

Thus, an amount increasing as the likelihood that the pixel of interest is a beam hardening artifact becomes higher and the CT value P becomes greater than the CT value corresponding to a soft part may be set as the amount of correction ΔP. Consequently, a rise of the CT value P due to partial bleeding or a local contrast effect may be appropriately kept. Similarly, bleeding or the contrast effect in a border between a bone part and a soft part, which is a somewhat smaller range, may be appropriately kept.

At Step S11, smoothing processing is performed. Specifically, the smoothing processing section 78 applies smoothing processing to a spatial distribution of the amount of correction ΔP determined at Step S10.

At Step S12, the CT value P is additionally corrected. Specifically, the CT-value correcting section 80 shift-corrects the CT value P using the smoothing-processed amount of correction ΔP for each pixel in a region corresponding to soft tissue in the beam-hardening corrected tomographic image, as given by the equation below.

The following equation represents an exemplary formula for calculating the corrected CT value P':

$$P'(x, y) = \begin{cases} P(x, y) - \Delta P(x, y) & \text{if } \Delta P(x, y) < \Delta P\_cap(x, y) \\ P(x, y) - \Delta P\_cap(x, y) & \text{if } \Delta P\_cap(x, y) \leq \Delta P(x, y) \end{cases} \qquad (5\text{-}1)$$

At Step S13, an additionally corrected tomographic image is displayed. Specifically, the display control section 81 controls the display device 62 to display on its screen the additionally corrected tomographic image obtained by the additional correction on the CT value P at Step S12.

Now exemplary tomographic images obtained by the method proposed herein will be demonstrated.

Figure 15:
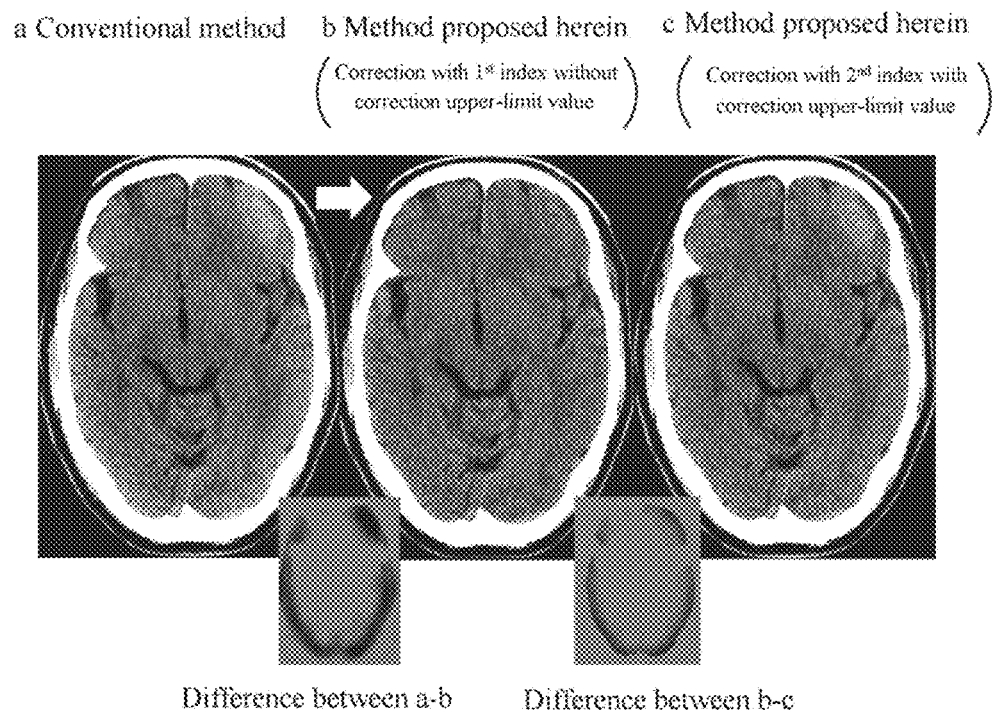
FIG. 15 A graphical depiction showing a result of comparison between a head tomographic image by the conventional method and that by the method proposed herein.

FIG. 15 is a graphical depiction showing a result of comparison between a head tomographic image by the conventional method and that by the method proposed herein. In the head tomographic image (left picture) according to the conventional method, a rise of the CT value due to undercorrection of beam-hardening correction may be recognized in a border between a bone part (skull) and soft tissue (cerebral tissue). On the other hand, in the head tomographic image (right picture) according to the method proposed herein, a state in which the rise of the CT value due to undercorrection is suppressed and improved may be recognized.

Figure 16:
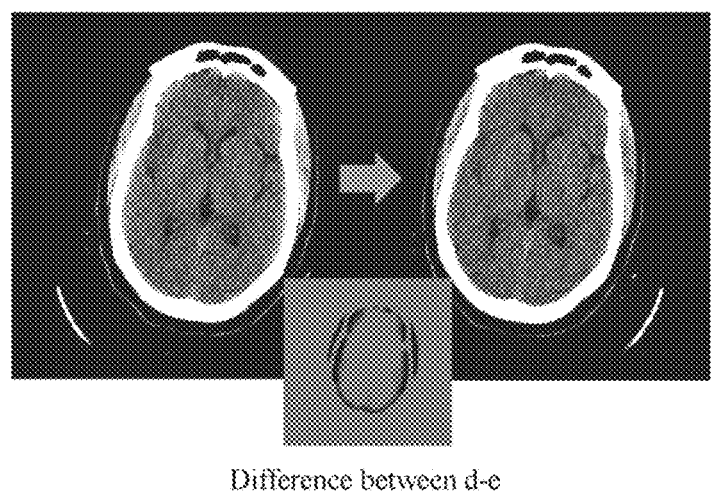
FIG. 16 A graphical depiction showing another result of comparison between a head tomographic image by the conventional method and that by the method proposed herein.

FIG. 16 is a graphical depiction showing another result of comparison between a head tomographic image by the conventional method and that by the method proposed herein. Of the three images, the left one is a head tomographic image according to the conventional method, the middle one is a head tomographic image according to the method proposed herein, where an amount of correction according to the first index is determined and no correction upper-limit value is defined, and the right one is a head tomographic image according to the method proposed herein, where an amount of correction according to the second index is determined and a correction upper-limit value is defined. In the head tomographic image (left image) according to the conventional method, a rise of the CT value due to undercorrection of beam-hardening correction is recognized in a border between a bone part (skull) and soft tissue (cerebral tissue). In the head tomographic image (central image) according to the method proposed herein and with no correction upper-limit value defined, although undercorrection of beam-hardening correction is improved, a rise of the CT value due to bleeding in the upper right portion is lost. On the other hand, in the head tomographic image (right picture) according to the method proposed herein and with a correction upper-limit value defined, undercorrection of beam-hardening correction is improved, and moreover, a rise of the CT value due to partial bleeding is kept.

As described above, according to the present embodiment, in a beam-hardening correction-processed head tomographic image, each individual pixel is sequentially defined as a pixel of interest, and a first index indicating how much beam hardening due to a bone part affects the pixel of interest is obtained based on CT values at a plurality of positions surrounding the defined pixel of interest and a distance from the pixel of interest, an amount of correction on the CT value for the pixel of interest is determined using the first index for the pixel of interest, and the CT value of the pixel of interest is corrected according to the amount of correction; therefore, for a portion in which mere conventional beam-hardening correction processing in a projection data space cannot fully correct the effect, the degree of the effect of beam hardening may be estimated with reference to information on the amount or closeness of the bone part present in the surrounding portion, and additional correction may be further applied to the CT value using a result of the estimation, so that variability in the result of correction by beam-hardening correction may be reduced in the head tomographic image.

In the present embodiment, in a pixel row containing the pixel of interest, a second index indicating a height of correlation between a positional change of the first index and a positional change of a differential CT value, which is a difference between the CT value and a reference CT value for soft tissue, is calculated, an amount of correction is determined according to the second index, and the CT value of the pixel of interest is corrected; therefore, the second index may be used as a degree of certainty that the pixel of interest is a beam hardening artifact, and additional correction may be applied to the CT value according to the degree of certainty, so that more correction may be performed on a region in which conventional beam-hardening correction causes undercorrection.

Moreover, since in the present embodiment, a correction upper-limit value according to the magnitude of the first index is defined for each pixel of interest, a risk of a side effect due to additional correction may be reduced, so that correction may be performed with higher accuracy while keeping partial bleeding or a local contrast effect caused by a contrast medium or the like and without loosing them.

It should be noted that the invention is not limited to the embodiment described above, and several modification may be made within the scope not departing from the spirit of the invention.

For example, while in the present embodiment, in obtaining the indices or in correcting the CT value, such a process is performed focusing upon a region corresponding to a single pixel as one unit, it may be applied to a subregion comprised of a plurality of pixels, for example, to an image region consisting of 2-by-2 pixels in longitudinal and horizontal directions as one unit.

Moreover, for example, while in the present embodiment, the body region to be imaged is the head, it may be any body region insofar as a bone part and soft tissue are contained therein.

Furthermore, while the present embodiment is an X-ray CT apparatus, the invention is also applicable to a tomographic imaging apparatus using radiation other than X-rays, for example, that using gamma rays.

In addition, a program for causing a computer to function as several means for performing control and/or processing in the X-ray CT apparatus described above and a recording medium in which such a program is stored each represent an exemplary embodiment of the invention.

The invention claimed is:

1. An image processing method causing a computer to execute:
   a first-index calculating step of generating, for a pixel of interest in a beam-hardening correction-processed computed tomography (CT) image representing a body region including a bone part and a soft tissue part, a first index estimating an amount of beam hardening experienced by the pixel of interest, wherein the first index is a sum of multiplied values derived from pixel-values of pixels surrounding the pixel of interest and respective distances of the pixels from the pixel of interest, and the pixel of interest is located in the soft tissue part and the pixels surrounding the pixel of interest are located in the bone part;
   a determining step of determining an amount of correction on a pixel-value for the pixel of interest using the first index for the pixel of interest;
   a pixel-value correcting step of correcting the pixel-value of the pixel of interest according to the amount of correction on the pixel of interest; and
   a displaying step of displaying an additionally corrected CT image with the pixel-value of the pixel of interest corrected.

2. An image processing apparatus comprising:
   a first-index calculating component configured to generate, for a pixel of interest in a beam-hardening correction-processed computed tomography (CT) image representing a body region including a bone part and a soft tissue part, a first index estimating an amount of beam hardening experienced by the pixel of interest, wherein the first index is a sum of multiplied values derived from pixel-values of pixels surrounding the pixel of interest and respective distances of the pixels from the pixel of interest, and the pixel of interest is located in the soft tissue part and the pixels surrounding the pixel of interest are located in the bone part;
   a correction determining component configured to determine an amount of correction on a pixel-value for the pixel of interest using the first index for the pixel of interest;

a pixel-value correcting component configured to correct the pixel-value of the pixel of interest according to the amount of correction on the pixel of interest; and a display configured to display an additionally corrected CT image with the pixel-value of the pixel of interest corrected.

3. The image processing apparatus as recited in claim 2, further comprising:

a differential pixel-value calculating component configured to generate, for the pixel of interest, a difference between the pixel-value of the pixel of interest and a reference value for pixel-values representing the soft tissue part; and a second-index calculating component configured to generate, for the pixel of interest, a second index indicating a degree of a correlation between a change of the first index in a direction passing through the pixel of interest and a change of the difference in the direction, wherein the differential pixel-value calculating component determines an amount of correction on the pixel-value for the pixel of interest based on the second index for the pixel of interest.

4. The image processing apparatus as recited in claim 3, wherein the correction determining component determines as the amount of correction a product of a value according to the second index for the pixel of interest and the difference for the pixel of interest.

5. The image processing apparatus as recited in claim 4, wherein the reference value for pixel-values representing the soft tissue part is an average of pixel-values in a region representing the soft tissue part in the image.

6. The image processing apparatus as recited in claim 4, wherein the reference value for pixel-values representing the soft tissue part is a representative value of pixel-values considered to correspond to the soft tissue part.

7. The image processing apparatus as recited in claim 3, further comprising:

a first smoothing processing component configured to apply smoothing processing to a distribution of the first index in the image and a distribution of the difference in the image, wherein the second-index calculating component generates the second index based on a correlation between a change of the first index to which the smoothing processing has been applied in the direction and a change of the difference to which the smoothing processing has been applied in the direction.

8. The image processing apparatus as recited in claim 7, wherein the second-index calculating component generates the second index so that it has a greater value for higher the correlation.

9. The image processing apparatus as recited in claim 2, further comprising:

a correction upper-limit value determining component configured to determine an upper-limit value of the amount of correction for the pixel of interest according to a magnitude of the first index for the pixel of interest, wherein the pixel-value correcting component corrects the pixel-value of the pixel of interest so that the amount of correction does not exceed an upper-limit value determined for the pixel of interest.

10. The image processing apparatus as recited in claim 2, further comprising:

a second smoothing processing component configured to apply smoothing processing to a distribution of the amount of correction in the image, wherein the pixel-value correcting component makes a correction using an amount of correction to which the smoothing processing has been applied.

11. The image processing apparatus as recited in claim 2, wherein the image is an image reconstructed based on projection data for the body region to which beam-hardening correction processing has been applied.

12. The image processing apparatus as recited in claim 2, wherein the beam-hardening correction processing uses an algorithm designed to correct beam hardening due to the bone part.

13. The image processing apparatus as recited in claim 2, wherein the body region is a head.

14. A computed tomographic (CT) imaging apparatus comprising:

an X-ray source configured to emit X-rays;

an X-ray detector facing the X-ray source and configured to generate signals in response to X-rays incident on the X-ray detector; and an operation console, comprising:

a first-index calculating component for generating, for a pixel of interest in a beam-hardening correction-processed CT image representing a body region including a bone part and a soft tissue part, a first index estimating an amount of beam hardening experienced by the pixel of interest, wherein the first index is a sum of multiplied values derived from pixel-values of pixels surrounding the pixel and respective distances of the pixels from the pixel of interest, and the pixel of interest is located in the soft tissue part and the pixels surrounding the pixel of interest are located in the bone part;

a correction determining component for determining an amount of correction on a pixel-value for the pixel of interest using the first index for the pixel of interest;

a pixel-value correcting component for correcting the pixel-value of the pixel of interest according to the amount of correction on the pixel of interest; and a display configured to display an additionally corrected CT image with the pixel-value of the pixel of interest corrected.

15. The CT imaging apparatus of claim 14, wherein the operation console further comprises:

a differential pixel-value calculating component for obtaining, for pixel, a difference between the pixel-value of the pixel of interest and a reference value for pixel-values representing the soft tissue part; and a second-index calculating component for generating, for the pixel of interest, a second index indicating a degree of a correlation between a change of the first index in a direction passing through the pixel of interest and a change of the difference in the direction, wherein the differential pixel-value calculating component determines an amount of correction on the pixel-value for the pixel of interest based on the second index for the pixel of interest.

16. The CT imaging apparatus of claim 15, wherein the operation console further comprises:

a first smoothing processing component for applying smoothing processing to a distribution of the first index in the image and a distribution of the difference in the image, wherein the second-index calculating component generates the second index based on a correlation between a change of the first index to which the smoothing processing has been applied in the direction and a change of the difference to which the smoothing processing has been applied in the direction.

* * * * *